United States Patent [19]

Barone

[11] 4,098,817

[45] Jul. 4, 1978

[54] OXIDATION OF CYCLOALIPHATIC COMPOUNDS

[75] Inventor: Bruno J. Barone, Houston, Tex.

[73] Assignee: Petro-Tex Chemical Corporation, Houston, Tex.

[21] Appl. No.: 97,317

[22] Filed: Dec. 11, 1970

[51] Int. Cl.² .............................................. C07C 51/00
[52] U.S. Cl. ............................ 260/533 C; 260/586 P; 260/531 R
[58] Field of Search ............ 260/533 C, 586 B, 531 R

[56] References Cited

U.S. PATENT DOCUMENTS

| 2,589,648 | 3/1952 | Wadsworth | 260/533 C |
| 2,675,407 | 4/1954 | Gallo | 260/533 C |
| 2,831,024 | 4/1958 | Brown et al. | 260/533 C X |
| 3,231,608 | 1/1966 | Kollar | 260/533 C |
| 3,383,413 | 3/1968 | Jaffe | 260/586 B X |
| 3,506,709 | 4/1970 | Nakamura | 260/533 C |

*Primary Examiner*—Paul J. Killos
*Attorney, Agent, or Firm*—Kenneth H. Johnson

[57] ABSTRACT

Cyclic compounds, particularly cycloalkanes and cycloalkenes can be oxidized using known metal oxidation catalysts in an organic ester solvent with considerable advantage over prior art solvents. For example cyclohexane was oxidized with a combination cobalt-manganese catalyst at a conversion of 15.3 mole % to give 20.3 mole % selectivity to adipic acid. Although this is not particularly high, 70.9 mole % of the converted cyclohexane was precursors of adipic acid which on recycle to the oxidation at a conversion of 14.4 mole % (total reaction time 0.23 hours) gave 64.6 mole % selectivity to adiptic acid and a total selectivity to adipic acid and precursors of 89.2 mole %.

1 Claim, No Drawings

OXIDATION OF CYCLOALIPHATIC COMPOUNDS

The present invention relates to the oxidation of cycloaliphatic compounds. More particularly the invention concerns the partial catalytic oxidation of saturated and monounsaturated cycloaliphatic compounds to dibasic acids in a single step process.

Prior processes in this field of catalytic oxidation of cycloaliphatic compounds have proposed the oxidation in the presence or absence of a solvent, by means of molecular oxygen and using various metals or salts thereof as catalysts. Usually solvents such as organic acids, halogenated or nitro aromatics are employed.

Generally, the prior art processes for the direct oxidation of cycloaliphatic compounds involve inherent disadvantages of low yields of the desired products and a variety of oxidized by-product in substantial quantities the removal of which may be difficult and require additional steps and expense. The by-products are often oxidized to the point of substantial uselessness, e.g. to carbon dioxide. Where the desired product was a dibasic acid, the prior art process generally required successive steps, as for example, first conversion of cyclohexane by catalytic air oxidation to cyclohexanone and cyclohexanol followed by the nitric acid oxidation of these precursors to adipic acid. The selectivity of cyclohexanone and cyclohexanol to adipic acid is high, however, degradation of the nitric acid to $N_2$ and $N_2O$ contributes significantly to the cost of making adipic acid by this route.

One object of the present invention is the provision of a novel process for the economical and efficient conversion of cycloaliphatic compounds to useful products such as adipic acid, azelaic acid and other such compounds. A further object is to provide a method having a single step whereby cycloaliphatic compounds may be directly oxidized to the desired products without the necessity of multiple steps and intermediate products or the combination of diverse oxidations. A still further object is to provide a method of carrying out such oxidations under relatively mild temperature conditions at either atmospheric or superatmospheric pressures so as to produce good yields of the desired product. Further, it is an object to produce low quantities of degraded by-products such as carbon dioxide. It is further an object to provide a process which goes to completion quickly and which also results in high yields of high purity product, and to provide a process wherein the principal by-products are precursors of the desired product and as such can be recycled to the oxidation to further improve the overall yield. These and other objects will become clear from the following description of the invention.

Briefly stated, the present invention is a process for partial oxidation comprising reacting saturated and monounsaturated cycloaliphatic compounds in an organic ester solvent with molecular oxygen at a temperature of 70° to 160° C. in the presence of a catalytic amount of a metal ion selected from the group consisting of Co, Mn, Ni, Cu, Zr, Ti, Hf, Nb, V, Ta, Mo, Zn and mixtures thereof.

Typical cycloaliphatic starting materials have 5 to 20 carbon atoms. In addition to carbon atoms the cycloaliphatic compounds can contain substituents which are non-reactive under the conditions. Such non-reactive substituents include halogens, particularly chlorine, bromine and fluorine, oxo, methoxy, carboxy, alkoxy, aryloxy, tertiary alkyl groups, nitro groups and the like. Generally, no more than 25% of the labile hydrogen will be substituted. The presence of hydrocarbon substituents on the ring is to be avoided since such alkyl groups, with the exception of tertiary groups, are usually easily oxidized and will detract from the oxidation of the ring. A preferred class of starting material is unsubstituted cycloalkanes or cycloalkenes having 5 to 20 carbon atoms. Specific examples of suitable cycloalkanes and cycloalkenes are cyclopentane, cyclopentene, cyclohexane, cyclohexene, cycloheptane, cycloheptene, cyclooctane, cyclooctene, cyclononane, cyclodecane, cycloundecane, cyclododecane, cyclododecene, cyclotridecane, cyclotetradecane, cyclopentadecane, cyclohexadecane, cyclohexadecene, cycloheptadecane, cyclooctadecane, cyclononadecane, cycloeicosene and the like. A few examples of suitable substituted cycloaliphatic compounds are cyclopentane carboxylic acid, chlorocyclopentane, 3-chlorocyclohexene, chlorocyclohexane, 1,3-dibromocyclohexane, fluorocyclohexane, cyclohexane carboxylic acid, nitrocyclohexane, 1,3-dinitrocyclohexane, oxomethoxycyclohexane, 4-chlorocyclohexanol, chlorocyclononane, 4-nitrocyclooctene and the like. Some preferred starting materials, principally because of the economic importance of the oxidation products are cyclohexane, cyclohexene, cyclooctane, cyclooctene, cyclononane, cyclononene, cyclodecane, cyclodecene, cyclododecane, and cyclododecene. The cycloaliphatic compound is generally present at a concentraton of about 1.0 to 10.0 molar usually less than 8.0 molar and above 3.0. Concentrations around 5.0 molar have been found to give excellent results. Concentrations above 5.0 molar exhibited longer reaction times and lower overall selectivity to the diacid and its precursor, although selectivity to diacid alone may increase. Concentrations below 5.0 molar gave respectable selectivities to the desired products although of a lower degree.

Typical reactions which illustrate the nature of the present oxidations are cyclopentane to cyclopentanone, cyclopentanol and glutaric acid; cyclohexane to cyclohexanone, cyclohexanol and adipic acid; cyclooctane to cyclooctanone, cyclooctanol and suberic acid; cyclodecane to cyclodecanone, cyclodecanol and sebacic acid; cyclododecane to cyclododecanone, cyclododecanol and 1,12-dodecanedioic acid; cyclotetradecane to cyclotetradecanone, cyclotetradecanol and tetradecanedioc acid; cyclohexadecane to cyclohexadecanone, cyclohexadecanol and thapsic acid; cyclooctadecane to cyclooctadecanone, cyclooctadecanol and octadecanedioic acid and the like.

The metal oxidation catalysts are generally those useful in this type of oxidation. Generally these metals can be described as having at least one valance of greater than +1 and are found in Period Table Groups IVB, VB, VIIB, VIII, IB and IIB. More specifically the catalyst is an ion of Co, Mn, Ni, Cu, Zr, Ti, Hf, Nb, V, Ta, Mo, Zn or mixtures of these metals. Of particular interest are CO, Mn, Cu, Zr and mixtures of these metals. It has been found, for example, in carrying out the process of the invention that a combination of Co and Mn ions produces better overall results than either Co or Mn alone. It has been found that in the present process it is possible to employ much smaller quantities of catalyst than generally employed in similar types of oxidations. The quantity of catalyst employed will usually be about 0.001 to 0.5 gram atom per mole of cycloaliphatic compound. Preferably about 0.002 to 0.2 gram atom of catalyst per mole of cycloaliphatic compound will be used. The metals or mixtures thereof may be in the form of salts, oxides, hydroxides and complexes, the only requirement being that sufficient amounts of the specified elements be present to provide a catalytic amount of ions in the solution during the course of the reaction. For example, the metal ions may be added in the form of compounds or complexes such as oxalates, naphthanates, sulfonates, acetylacetonates, alcoholates, chloride octoates, acetylacetates, and the like. Salts of the lower fatty acids are especially useful, e.g., acetates, propionates, and butyrates.

A significant feature of the invention is the use of a particular type of solvent. As stated previously the solvent is an organic ester. The term "organic ester" is understood to mean the condensation product of an organic acid and an organic alcohol. Suitable esters would have the formula selected from the group consisting of

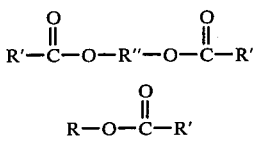

and

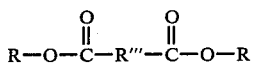

where each R is an organic radical comprising 1 to 12 carbon atoms, each R' is independently selected from the group consisting of hydrogen and an organic radical comprising 1 to 11 carbon atoms, R" is an organic radical comprising 2 to 12 carbon atoms and R'" is nonexistent or an organic radical comprising 1 to 10 carbon atoms. In addition to hydrogen the organic radicals represented by R, R', R" and R'" can have substituted thereon groups which are nonreactive under the conditions such as halogen, e.g., bromine, chlorine and fluoride, nitro, hydroxy, tertiary alkyl and the like. Generally such substituents will replace less than 25% of the labile hydrogen in any of said organic radicals. The organic radicals of the esters can be aliphatic, cycloaliphatic or aromatic. The esters will not contain ethylenic unsaturation since such sites are reactive in the conditions of the reaction. A particularly useful group of ester solvents are those where the alcohol and acid portions are both hydrocarbons, i.e., the organic radicals are hydrocarbon radicals.

The esters of course can be used singularly or in admixture. The preparation of organic esters is well known technology and forms no part of this invention. Large numbers and varieties of organic esters are commercially available, others can be readily produced by conventional esterification processes. Some suitable ester solvents include: ethyl-1,2-diformate; ethyl-1,2-diacetate; ethyl-1,2-dipropionate; propyl-1,3-dibutyrate; phenyl-1,5-dicyclohexane carboxylate; octyl-1-formate-8-benzoate; dodecyl-1-cyclopentane carboxylate-12-benzoate; ethyl-1-formate-2-(naphthalene-2-carboxylate); ethyl-1-acetate-2-laurate; cyclohexyl-1,4-diformate; cyclodecyl-1-acetate-6-cyclohexyl carboxylate; cyclodecyl-1,2-dicyclobutyrate; cyclohexyl-1-formate-4-naphthanate; benzyl-1,4-diformate; benzyl-1-acetate-3-cyclohexane carboxylate; benzyl-1,4-dibenzoate; methyl formate; methyl acetate; ethyl formate; ethyl acetate; butylacetate; n-amyl valerate; hexyl nonanate, isopropyl benzoate; isobutyl benzoate; octyl laurate; methyl benzoate; ethyl benzoate; 6-butyl naphthalene-2-carboxylate; 1-ethyl cyclobutane-2-carboxylate; 1-heptyl cyclohexane-3-carboxylate; cyclopentyl acetate; cyclohexyl laurate; 1-cyclododecyl-cyclobutane-2-carboxylate; cyclodecyl benzoate; benzyl formate; benzyl acetate; benzyl cyclopropane carboxylate; toluyl laurate; toluyl cyclohexane carboxylate; toluyl benzoate; benzyl naphthalene-2-carboxylate; dimethyl oxalate; diethyl malonate; methyl, hexyl succinate; propyl, octyl suberate; diethyl laurate; methyl, cyclopentyl oxalate; ethyl, cyclododecyl pimelate; cyclohexyl, benzyl glutarate; benzyl, toluyl suberate; methyl, (2-naphthyl) suberate; dimethyl-1,2-cyclopropane dicarboxylate; ethyl, cyclohexyl-1,2-cyclobutane dicarboxylate; dicyclohexyl-1,3-cyclopentane dicarboxylate; methyl, cyclodecyl-1,4-cyclohexane dicarboxylate; benzyl, cyclopentyl-1,4-cyclohexane dicarboxylate; methyl, toluyl-1,3-cyclopentane dicarboxylate; dimethyl-1,3-benzene dicarboxylate; methyl, ethyl-1,4-benzene dicarboxylate; dodecyl, methyl-1,6-naphthalene dicarboxylate; cyclohexyl, ethyl-1,4-benzene dicarboxylate; dibenzyl-1,4-benzene dicarboxylate; 2-chloro propyl-1,3-dibutyrate; (4,5-dibromo dodecyl)-1-cyclopentane carboxylate-12-benzoate; 2-nitrocyclohexyl-1,4-diformate; 2,4-dinitrobenzyl-1,3-diacetate; and the like.

A particularly suitable ester solvent is one of the structure

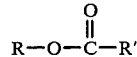

where R is $C_1$ to $C_4$ and R' is hydrogen or $C_1$ to $C_3$.

The principal requisites for the ester solvent are being liquid and inert under the reaction conditions. Preferably the esters are liquid at room temperature, which will facilitate handling and separation of the products therefrom. It is also advantageous if the ester can be selected so that the desired product, for example, a diacid is insoluble in the solvent at room temperature and can be removed by filtration.

The solvent can be employed at a very wide optional ratio to the substance being oxidized, generally the solvent which may be a mixture of esters or a single ester will be present at from about 0.3 to 10 moles per liter of solution. Some preferred solvents are methyl acetate, ethyl acetate, cyclohexyl acetate, cyclododecyl acetate, methyl propionate, isopropyl acetate, n-propyl acetate, ethyl oxalate, methyl succinate or mixtures thereof.

A principal feature of the present invention is high selectivity of the process to the desired oxidation products. That is, there is very little destruction of the hydrocarbon chain of the starting material so that the products are principally the dibasic acids of the scissioned cyclic starting material or precursors of the dibasic acid. Thus the desired product, for example, the diacid can be removed and the bulk of the remaining lesser oxidized by-products recycled to the same oxidation to produce more of the diacid. Generally, the prior art processes for this type of oxidation were not suited to oxidize the unoxidized starting material as well as the partially oxidized analogues, e.g., cyclohexane, cyclohexanol, cyclohexnone, 6-hydroxy caproic acid and ε-caprolactone. This is not to imply that no prior single reaction could not oxidize all of these materials in their various stages of oxidation, but the net result would be lower selectivities to the desired products. Generally the prior art oxidations gave relative high yields of carbon dioxide and/or mixtures of oxidation products which were the result of multiple scissions of the carbon chain of the starting material.

It has been found that the use of the organic ester solvents described above by some yet unexplained mechanism moderates and facilitates the oxidation of the carbon chain of the cyclic starting material to produce fewer by-products other than the precursors of the single scission diacids. The solvent has allowed the use as pointed out above of lower catalyst concentrations and even lower solvent concentrations than generally taught in the prior art processes.

Although there is much emphasis here in regard to diacid products, it is entirely possible that the desired oxidation product will be one of the less oxidized precursors thereof and the instant process can be carried out so as to maximize such a lesser oxidized product by reduction or elimination of recycle, lower reaction temperatures, shorter reaction times and other mere mechanical manipulations which will be more evident from the examples.

The products of the present reaction have numerous uses. For example adipic acid is used in the preparation of nylon. The fatty acids generally can be used in production of various polyamides, polyamines and polyesters as either the principal dibasic component or as modifying agents. The fatty acids of 5-20 carbon atoms have almost endless uses in chemical technology as intermediates, for example, conversion to amines which are surface active agents and so forth. The less oxidized products also have multiple uses, for example, alcohols and ketones are excellent solvents.

The process can be carried out at temperatures of about 70° to 160° C., generally the temperature will be about 90° to 140° C. The process can be operated at atmospheric pressure but generally is operated at super atmospheric pressure in order to maintain the reactants, solvents, products, etc. in liquid phase. The amount of pressure will usually be that sufficient to maintain the liquid phase and e.g. up to about 50 atmospheres.

The molecular oxygen employed can be in the form of pure oxygen or oxygen diluted with inert gases such as nitrogen or helium. Air has been found a suitable source of molecular oxygen. The oxygen is fed to the reaction in the range of about 1 to 1,000 moles per mole of material to be oxidized, preferably about 5 to 100 moles per mole of material to be oxidized. The process of the invention can be carried out continuously or batchwise with or without recycle employing conventional equipment, however, since the products include organic acids precautions must be taken to avoid corrosion, for example, reactor, distillation columns, filter screens and the like can be constructed of stainless steel or glass coated steel.

The following examples are intended to illustrate the invention. The examples particularly illustrate the effect of the variables previously discussed and no limitation to the subject matter of the specific examples is intended or should be implied therefrom.

The reactor used in the examples was a 3,000 p.s.i. magnetically stirred 1.4 liter autoclave equipped with a Dispersamax agitator, reflux condenser and internal water cooling coil. Inlet gas was measured by following the pressure drop in a standardized metering vessel and fed into the autoclave through a ballast type pressure regulator. Exit gas was controlled with a metering needle valve located after the condenser.

The reaction mixture was analyzed by gas chromatography using the peak area method with appropriate predetermined factors and by use of an internal standard. Unreacted starting material, e.g., cyclohexane and low boiling products were determined using a Perkin Elmer Model 154C gas chromatograph and helium flow. Other products were determined using isopropanol as an internal standard. For this purpose as F and M 720 dual column gas chromatograph was used with a helium flow.

EXAMPLES 1-3

These examples demonstrate the effect of solvent concentration over a wide range, i.e., from 0.65 to 6.94 moles/liter of solution on the oxidation of cyclohexane. Table I gives the reactants, conditions and results. Note that the effect on the product is less than would be expected over such a broad range of feed dilution. Low carbon dioxide by-product resulted in each run. It can be seen that the total adipic acid and precursor selectivity of examples 1 and 3 are of the same order whereas run 2 represents a more optimal set of conditions within the two extremes.

TABLE I

Oxidation of Cyclohexane in Ethyl Acetate Solvent At 130° C Under 300 PSI Oxygen Pressure (Effect of Ethyl Acetate Concentration)

| Example No. | 1 | 2 | 3 |
|---|---|---|---|
| Reactants | | | |
| Cyclohexane, M/L | 8.7 | 5.0 | 3.0 |
| Ethyl Acetate, M/L | 0.65 | 4.73 | 6.94 |
| Cobaltic Acetylacetonate, M/L | 0.007 | 0.007 | 0.007 |
| Reaction Conditions | | | |
| Total Reaction Time, hrs. | 1.42 | 0.6 | 0.63 |
| Results | | | |
| Induction Period, min. | 4.5 | 19 | 15.5 |
| Oxygen Consumed, M/L | 0.978 | 1.105 | 0.654 |
| Carbon Dioxide Produced, M/L | 0.350 | 0.094 | 0.176 |
| Cyclohexane Consumed, % | 9.6 | 18.1 | 14.2 |
| % Selectivity | | | |
| Adipic Acid | 19.0 | 16.2 | 15.1 |
| Glutaric Acid | 5.1 | 0.3 | 0.5 |
| Succinic Acid | 2.2 | 3.3 | 4.7 |
| Cyclohexanone | 33.1 | 43.1 | 43.0 |
| Cyclohexanol | 29.1 | 20.5 | 14.7 |
| 6-Hydroxy Caproic | 2.6 | 13.2 | 10.2 |
| ε-Caprolactone | 2.1 | 1.8 | 2.0 |
| Total Adipic + Precursor | 86.0 | 94.8 | 85.0 |

EXAMPLES 4-7

These examples demonstrate the process using methyl acetate or t-butyl acetate as the solvent with cobalt or manganese ions as the catalyst. Conditions, reactants and results are in Table II.

TABLE II

Oxidation of Cyclohexane in an Ester Solvent Under 300 PSI Oxygen Pressure

| Example | 4 | 5 | 6 | 7 |
|---|---|---|---|---|
| Reactants | | | | |
| Cyclohexane, M/L | 8.0 | 8.0 | 5.0 | 8.0 |
| Methyl Acetate, M/L | 1.8 | — | 6.06 | 1.8 |
| t-Butyl Acetate, M/L | — | 1.07 | — | — |
| Cobaltic Acetylacetonate, M/L | 0.007 | 0.007 | 0.007 | — |
| Manganic Acetylacetonate MlL | — | — | — | 0.007 |
| Reaction Conditions | | | | |
| Total Reaction Time, hrs. | 2.3 | 1.5 | 2.3 | 0.83 |
| Temperature, ° C | 120 | 300 | 120 | 130 |
| Results | | | | |
| Induction Period, min. | 15 | 33.5 | 40 | 33 |

TABLE II-continued

Oxidation of Cyclohexane in an Ester Solvent Under 300 PSI Oxygen Pressure

| Example | 4 | 5 | 6 | 7 |
|---|---|---|---|---|
| Oxygen Consumed, M/L | 0.891 | 0.960 | 1.54 | 1.044 |
| Carbon Dioxide Produced, M/L | 0.174 | 0.404 | 0.239 | 0.134 |
| Cyclohexane Consumed, % | 11.4 | 16.5 | 23.3 | 11.6 |
| % Selectivity | | | | |
| Adipic Acid | 15.6 | 14.0 | 18.3 | 16.2 |
| Glutaric Acid | 1.8 | 3.5 | 1.1 | 1.1 |
| Succinic Acid | 1.5 | 1.8 | 2.2 | 0.8 |
| Cyclohexanone | 37.6 | 28.0 | 35.5 | 24.9 |
| Cyclohexanol | 30.8 | 23.3 | 25.7 | 28.9 |
| 6-Hydroxy Caproic Acid | 5.3 | 5.1 | 8.9 | 8.9 |
| ε-Caprolactone | 1.6 | 1.0 | 1.3 | .7 |
| Total Adipic + Precursors | 93.9 | 71.1 | 89.7 | 80.6 |

EXAMPLES 8-13

These examples show the use of recycle at two different catalyst (cobalt acetate) concentrations. It can be seen that total selectivity to the desired diacid (adipic) and its precursors remained above 80% in all runs while the selectivity to adipic acid increased over 50% in each recycle. The conditions, reactants and results are in Table III.

TABLE III

Cobaltous Acetate Catalyzed Oxidation of 5.0 Molar Solution of Cyclohexane In Ethyl Acetate at 130° C. Under 300 PSI Oxygen Pressure

| | Recycle Activity - 0.00 M/L Cobalt Catalyst | | | Recycle Activity - 0.005 M/L Cobalt Catalyst | | |
|---|---|---|---|---|---|---|
| Example | 8 | 9 | 10 | 11 | 12 | 13 |
| Note: | | (a) | (b) | | (c) | (d) |
| Reaction Conditions | | | | | | |
| Total Reaction Time, hrs. | 1.13 | 0.43 | 0.38 | 1.23 | 0.3 | 0.35 |
| Results | | | | | | |
| Oxygen Consumed, M/L | 1.095 | 1.099 | 1.078 | 1.098 | 1.115 | 1.060 |
| Carbon Dioxide Produced, M/L | 0.083 | 0.134 | 0.145 | 0.095 | 0.081 | 0.100 |
| Cyclohexane Consumed, % | 16.9 | 16.8 | 13.8 | 16.9 | 8.2 | 13.1 |
| % Selectivity | | | | | | |
| Adipic Acid | 18.2 | 29.5 | 31.3 | 21.6 | 32.1 | 31.9 |
| Glutaric Acid | 0.7 | 1.8 | 6.8 | 0.7 | 0.4 | 2.8 |
| Succinic Acid | 3.6 | 3.6 | 3.0 | 2.4 | 4.0 | 5.7 |
| Cyclohexanone | 34.6 | 50.1 | 23.4 | 38.7 | 39.5 | 34.5 |
| Cyclohexanol | 19.5 | 3.7 | 11.5 | 18.5 | 5.4 | 7.6 |
| 6-Hydroxy Caproic | 14.7 | 2.1 | 12.5 | 10.9 | 8.9 | 7.2 |
| ε-Caprolactone | 1.4 | 1.3 | 1.7 | 2.0 | 1.9 | 1.8 |
| Total Adipic + Precursors | 88.4 | 86.7 | 80.4 | 91.7 | 87.8 | 83.0 |

(a) Filtrate from 8 was reused in this run after reconstitution with cyclohexane and cobaltous acetate catalyst.
(b) Filtrate from 9 was reused in this run after reconstitution with cyclohexane and cobaltous acetate catalyst.
(c) Filtrate from 11 was reused after reconstitution with catalyst, ethyl acetate and cyclohexane.
(d) Entire filtrate from 12 was reused after reconstitution as in c.

EXAMPLES 14 and 15

These examples and Example 11 demonstrate the relatively wide range of catalyst concentrations that produce comparable results. The catalyst was cobaltous acetate and the starting material cyclohexane. The conditions, reactants and results are shown in Table IV.

TABLE IV

Oxidation of 5.0 Molar Solution of Cyclohexane in Ethyl Acetate at 130° C. Under 300 PSI Oxygen Pressure Effect of Cobalt Catalyst Concentration

| Example | 14 | 11 | 15 |
|---|---|---|---|
| Reactants | | | |
| Cobaltous Acetate . 4H$_2$O, M/L | 0.01 | 0.005 | 0.0025 |
| Reaction Conditions | | | |
| Total Reaction Time, hrs. | 1.07 | 1.23 | 1.27 |
| Results | | | |
| Induction Period. min. | 36 | 43 | 44 |
| Oxygen Consumed, M/L | 1.102 | 1.098 | 1.123 |
| Carbon Dioxide Produced, M/L | 0.119 | 0.095 | 0.080 |
| Cyclohexane Consumed, % | 17.5 | 16.9 | 15.3 |
| % Selectivity | | | |
| Adipic Acid | 18.9 | 21.6 | 19.9 |
| Glutaric Acid | 0.6 | 0.7 | 0.4 |
| Succinic Acid | 3.9 | 2.4 | 3.7 |
| Cyclohexanone | 39.8 | 38.7 | 38.0 |
| Cyclohexanol | 17.5 | 18.5 | 18.3 |
| 6-Hydroxy Caproic Acid | 12.9 | 10.9 | 12.8 |
| ε-Caprolactone | 2.4 | 2.9 | 1.2 |
| Total Adipic + Precursors | 91.5 | 91.7 | 90.2 |

EXAMPLES 16-19

Examples 16 and 17 show the use of manganese ion as the catalyst for oxidizing cyclohexane and recycle. Examples 18 and 19 show using a combination of manganese and cobalt and recycle. Examples 8 and 9 are added to Table V wherein 16-19 are set out in order to illustrate the improvement of the combined catalyst over either of the two components. Not only is there a good conversion in Examples 18 and 19 but high yield of adipic acid and precursors. The reaction time on the recycle (Example 19) was only 0.23 hours and the undesirable by-products $CO_2$, glutaric acid and succinic acid are very low. Reactants, conditions and results are set out in Table V.

TABLE V

Oxidation of Cyclohexane in Ethyl Acetate at 130° C. Under 300 PSI Pressure

| Run No. | 16 | 17 | 18 | 19 | 8 | 9 |
|---|---|---|---|---|---|---|
| Reactants | | | | | | |
| Cyclohexane, M/L | 5.0 | — | 5.0 | — | 5.0 | 5.0 |
| Ethyl Acetate, M/L | 4.73 | — | 4.73 | — | 4.73 | 4.73 |
| Manganous Acetate . 4H$_2$O, M/L | 0.01 | 0.005 | 0.005 | 0.005 | — | — |
| Cobaltous Acetate . 4H$_2$O, M/L | — | — | 0.005 | 0.005 | 0.01 | 0.01 |
| Reaction Conditions | | | | | | |
| Total Reaction Time, Hrs. | 1.9 | 0.47 | 1.48 | 0.23 | 1.13 | 0.43 |
| Results | | | | | | |

TABLE V-continued

Oxidation of Cyclohexane in Ethyl Acetate at 130° C. Under 300 PSI Pressure

| Run No. | 16 | 17 | 18 | 19 | 8 | 9 |
|---|---|---|---|---|---|---|
| Induction Period, min. | 78 | 20 | 53 | 8.5 | 38 | 5.2 |
| Oxygen Consumed, M/L | 1.089 | 0.691 | 1.003 | 1.315 | 1.095 | 1.099 |
| Carbon Dioxide Produced, M/L | 0.096 | 0.213 | 0.083 | 0.116 | 0.083 | 0.134 |
| Cyclohexane Consumed, % | 16.8 | 12.9 | 15.3 | 14.4 | 16.9 | 16.8 |
| Note: | | (a) | | (b) | | (c) |
| % Selectivity | | | | | | |
| Adipic Acid | 19.1 | 66.6 | 20.3 | 64.6 | 18.2 | 29.5 |
| Glutaric Acid | 1.2 | 9.8 | 0.6 | 6.2 | 0.7 | 1.8 |
| Succinic Acid | 1.7 | 1.9 | 1.6 | 2.0 | 3.6 | 3.6 |
| Cyclohexanone | 37.3 | 2.0 | 37.3 | 12.0 | 34.6 | 50.1 |
| Cyclohexanol | 21.7 | — | 19.2 | 3.8 | 19.5 | 3.7 |
| 6-Hydroxy Caproic Acid | 13.0 | 7.1 | 12.7 | 7.7 | 14.7 | 2.1 |
| ε-Caprolactone | 3.5 | 6.6 | 1.7 | 1.7 | 1.4 | 1.3 |
| Total Adipic + Precursors | 94.6 | 82.3 | 91.2 | 89.2 | 88.4 | 86.7 |

(a) Filtrate from 16 recycled after reconstitution with cyclohexane.
(b) Filtrate from 18 recycled after reconstitution with cyclohexane.
(c) Filtrate from 8 was reused in this after constitution with cyclohexane, and cobaltous acetate catalyst.

EXAMPLES 20–29

This set of examples demonstrate a number of additional metal ions used as the catalyst for the oxidation of cyclohexane. The reactants, conditions and results appear in Table VI.

TABLE VI

Oxidation of 5.0 Molar Solution of Cyclohexane in Ethyl Acetate Under 300 PSI Oxygen Pressure

| | Miscellaneous Catalyst Systems | | | | | | | | | |
|---|---|---|---|---|---|---|---|---|---|---|
| Example | 20 | 21 | 22 | 23 | 24 | 25 | 26 | 27 | 28 | 29 |
| Reactants | | | | | | | | | | |
| Nickel Acetate . 4H$_2$O, M/L | 0.01 | 0.01 | — | — | — | — | — | — | — | — |
| Cupric Acetate . H$_2$O, M/L | — | — | 0.013 | 0.013 | — | — | — | — | — | — |
| Zirconium Acetate, M/L | — | — | — | — | 0.0076 | 0.0076 | — | — | — | — |
| Molybdenyl Acetylacetonate, M/L | — | — | — | — | — | — | 0.008 | 0.008 | — | — |
| Zinc Acetyl Acetonate, M/L | — | — | — | — | — | — | — | — | 0.005 | 0.005 |
| Reaction Conditions | | | | | | | | | | |
| Temperature °C | 130 | 130 | 130 | 130 | 130 | 130 | 140 | 130 | 130 | 130 |
| Total Reaction Time, hrs. | 1.37 | 0.58 | 2.17 | 0.47 | 5.77 | 0.52 | 2.58 | 1.12 | 5.25 | 0.45 |
| Results | | | | | | | | | | |
| Induction Period, min. | 29 | 7 | 90 | 11 | 266 | 5.5 | 127 | 15.5 | 186 | 9.2 |
| Oxygen consumed, M/L | 0.970 | 1.048 | 0.995 | 1.024 | 0.705 | 1.005 | 1.033 | 1.165 | 1.010 | 1.040 |
| Carbon Dioxide Produced, M/L | 0.094 | 0.138 | 0.144 | 0.176 | 0.121 | 0.156 | 0.028 | 0.163 | 0.101 | 0.164 |
| Cyclohexane Consumed, % | 17.1 | 13.3 | 16.2 | 11.8 | 12.0 | 13.0 | 13.6 | 11.7 | 17.8 | 16.5 |
| Note: | | (a) | | (b) | | (c) | | (d) | | (e) |
| % Selectivities | | | | | | | | | | |
| Adipic Acid | 11.3 | 32.9 | 18.9 | 44.0 | 13.5 | 37.9 | 22.6 | 43.7 | 23.7 | 35.4 |
| Glutaric Acid | 1.6 | 0.8 | 1.3 | 2.2 | 0.9 | 1.8 | 0.6 | 4.2 | 1.2 | 1.6 |
| Succinic Acid | 1.7 | 1.5 | 2.1 | — | 1.9 | 2.0 | 0.6 | 1.8 | 1.1 | 2.6 |
| Cyclohexanone | 32.7 | 32.7 | 40.2 | 34.3 | 32.5 | 41.7 | 34.8 | 19.5 | 38.1 | 29.1 |
| Cyclohexanol | 20.8 | 3.4 | 19.5 | 1.6 | 25.8 | 4.5 | 16.3 | 0.6 | 16.3 | 0.7 |
| 6-Hydroxy Caproic Acid | 7.9 | 5.1 | 7.7 | 7.6 | 9.9 | 4.9 | 9.5 | 2.9 | 8.8 | 7.8 |
| εCaprolactone | 2.8 | 4.3 | 5.6 | 4.9 | 12.5 | — | 3.5 | 2.9 | 8.6 | — |

(a) Filtrate from 20 recycled after reconstitution with cyclohexane.
(b) Filtrate from 22 recycled after reconstitution with cyclohexane.
(c) Filtrate from 24 recycled after reconstitution with cyclohexane.
(d) Filtrate from 26 recycled after reconstitution with cyclohexane.
(e) Filtrate from 28 recycled after reconstitution with cyclohexane.

EXAMPLES 30–32

The process of Example 8 is carried out but with cyclododecene, cyclododecane and cyclooctadecane employed as the starting material. In the case of cyclododecene an equivalent conversion to that of Example 8 is obtained with a shorter reaction time. In each case selectivities to the desired diacid are of the same order as for cyclohexane as are total selectivities for the desired diacid and its precursors.

The invention claimed is:

1. A process for partial oxidation of cycloaliphatic compounds selected from the group consisting of cycloalkanes and cycloalkenes containing from 5 to 20 carbon atoms to produce acyclic diacids, cycloaliphatic ketones and cycloaliphatic alcohols having the same number of carbon atoms as said cycloaliphatic compounds, said cycloaliphatic compounds being unsubstituted or contain non-reactive ring substituents selected from the group consisting of tertiary alkyl groups, halogen, oxo, methoxy, carboxy, alkoxy, aryloxy and nitro groups, said process comprising reacting a solution of from about 1.0 to 10 molar of said cycloaliphatic compounds in organic ester solvent with molecular oxygen at a temperature of 70° to 160° C in the presence of a catalytic amount in the range of about 0.001 to 0.5 gram atom per mole of cycloaliphatic compounds of a catalyst consisting of Zr, wherein said organic ester solvent is selected from the group consisting of methyl acetate, ethyl acetate or t-butyl acetate, said organic ester solvent being present in an amount from about 0.3 to 10 moles per liter of solution.

* * * * *